US012678786B2

(12) United States Patent (10) Patent No.: US 12,678,786 B2
Lindblom et al. (45) Date of Patent: Jul. 14, 2026

(54) FLUIDIC DETECTION AND CONTROL ALGORITHM FOR PCR ANALYSIS

(71) Applicant: Formulatrix International Holding Ltd., Dubai (AE)

(72) Inventors: Rasmus Lindblom, Bedford, MA (US); Michael Nilsson, Bedford, MA (US)

(73) Assignee: Formulatrix International Holding Ltd., Dubai (AE)

( * ) Notice: Subject to any disclaimer, the term of this patent is extended or adjusted under 35 U.S.C. 154(b) by 520 days.

(21) Appl. No.: 18/032,457

(22) PCT Filed: Oct. 19, 2021

(86) PCT No.: PCT/US2021/055645
§ 371 (c)(1),
(2) Date: Apr. 18, 2023

(87) PCT Pub. No.: WO2022/086987
PCT Pub. Date: Apr. 28, 2022

(65) Prior Publication Data
US 2024/0002918 A1 Jan. 4, 2024

Related U.S. Application Data

(60) Provisional application No. 63/093,640, filed on Oct. 19, 2020.

(51) Int. Cl.
B01L 3/00 (2006.01)
B01L 7/00 (2006.01)
(Continued)

(52) U.S. Cl.
CPC ... B01L 3/502715 (2013.01); B01L 3/502761 (2013.01); B01L 7/52 (2013.01);
(Continued)

(58) Field of Classification Search
CPC ......... B01L 3/502715; B01L 3/502761; B01L 7/52; B01L 2200/027; B01L 2200/0668;
(Continued)

(56) References Cited

U.S. PATENT DOCUMENTS 5,912,129 A * 6/1999 Vinayagamoorthy .... B01L 7/52
435/6.12
2003/0129671 A1 7/2003 Wilding et al.
(Continued)

FOREIGN PATENT DOCUMENTS

CN 101903104 A 12/2010
CN 104981698 A 10/2015
(Continued)

*Primary Examiner* — Georgia Y Epps
*Assistant Examiner* — Don J Williams
(74) *Attorney, Agent, or Firm* — E. Eric Mills; Todd A. Serbin; Maynard Nexsen PC

(57) ABSTRACT

Disclosed are various embodiments for systems and methods for detecting and making real-time adjustments to positional control of a fluidic volume moving through an optical detection region in a fluidic channel of a chip on a RT-qPCR system. Said embodiments are disclosed within a RT-qPCR system having a chip and a cartridge for receiving the chip, and further a mechanical instrument for interacting with a membrane of the chip for positional control. Further, example embodiments include systems and methods for capacitive detection of a fluid within a fluidic channel as well as optical detection within an optical detection region of a fluidic channel within a chip.

21 Claims, 8 Drawing Sheets

(51) Int. Cl.
    *C12Q 1/6851*       (2018.01)
    *G01N 21/05*       (2006.01)

(52) U.S. Cl.
    CPC ........... *C12Q 1/6851* (2013.01); *G01N 21/05*
        (2013.01); *B01L 2200/027* (2013.01); *B01L*
        *2200/0668* (2013.01); *B01L 2200/10*
        (2013.01); *B01L 2200/16* (2013.01); *B01L*
        *2300/044* (2013.01); *B01L 2300/0654*
        (2013.01); *B01L 2300/0672* (2013.01); *B01L*
        *2300/0883* (2013.01); *B01L 2300/0887*
        (2013.01); *B01L 2300/123* (2013.01); *B01L*
        *2400/0403* (2013.01); *B01L 2400/043*
        (2013.01); *B01L 2400/0683* (2013.01)

(58) Field of Classification Search
    CPC ............. B01L 2200/16; B01L 2200/10; B01L
                2300/044; B01L 2300/0654; B01L
                2300/0672; B01L 2300/0883; B01L
                2300/0887; B01L 2300/123; B01L
                2400/0403; B01L 2400/043; B01L
            2400/0683; C12Q 1/6851; G01N 21/05
    See application file for complete search history.

(56) References Cited

U.S. PATENT DOCUMENTS

| | | | |
|---|---|---|---|
| 2006/0094004 | A1 | 5/2006 | Nakajima et al. |
| 2009/0042737 | A1* | 2/2009 | Katz ........................ B01L 7/525 |
| | | | 506/10 |
| 2010/0304986 | A1 | 12/2010 | Chen et al. |

| | | | |
|---|---|---|---|
| 2012/0122108 | A1 | 5/2012 | Handique |
| 2012/0152369 | A1 | 6/2012 | Hiddessen et al. |
| 2013/0252262 | A1 | 9/2013 | Srinivasan et al. |
| 2014/0141498 | A1 | 5/2014 | Enzelberger et al. |
| 2014/0272965 | A1 | 9/2014 | Handique et al. |
| 2015/0136602 | A1 | 5/2015 | Jovanovich et al. |
| 2015/0217293 | A1 | 8/2015 | Faulstich et al. |
| 2016/0296930 | A1 | 10/2016 | Matear et al. |
| 2017/0241949 | A1 | 8/2017 | Bort et al. |
| 2018/0372595 | A1 | 12/2018 | Pais et al. |
| 2019/0001325 | A1 | 1/2019 | Pais et al. |
| 2019/0256890 | A1 | 8/2019 | Eberhart et al. |
| 2019/0283024 | A1 | 9/2019 | Aravanis et al. |
| 2020/0269239 | A1 | 8/2020 | Johnson et al. |

FOREIGN PATENT DOCUMENTS

| | | |
|---|---|---|
| EP | 2437887 B1 | 5/2016 |
| EP | 3524973 A1 | 8/2019 |
| JP | H07/054776 A | 2/1995 |
| JP | H10196544 A | 7/1998 |
| JP | 2004309145 A | 11/2004 |
| JP | 2007101428 A | 4/2007 |
| JP | 2009509549 A | 3/2009 |
| JP | 2011501665 A | 1/2011 |
| JP | 2012/529268 A | 11/2012 |
| JP | 2014163773 A | 9/2014 |
| JP | 2016516195 A | 6/2016 |
| JP | 2017067595 A | 4/2017 |
| JP | 2017/522545 A | 8/2017 |
| JP | 2020073912 A | 5/2020 |
| JP | 2020517916 A | 6/2020 |
| WO | 2018022971 A1 | 2/2018 |
| WO | 2019045807 A1 | 3/2019 |

* cited by examiner

402

404

ADC COUNTS

TIME

512

506

508

502   510   502

502

502

502

504                    504

TRADITIONAL qPCR AMPLIFICATION CURVES
(60 MINUTES FOR 45 CYCLES)

DISCLOSED EMBODIMENT qPCR AMPLIFICATION CURVES
(10 MINUTES FOR 50 CYCLES)

FLUIDIC DETECTION AND CONTROL ALGORITHM FOR PCR ANALYSIS

CROSS REFERENCE TO RELATED APPLICATIONS

This application is a 35 U.S.C. § 371 U.S. national phase entry of International Application No. PCT/US2021/055645 having an international filing date of Oct. 19, 2021, which claims the benefit of priority under Article 8 PCT of U.S. Provisional Patent Application No. 63/093,640 filed Oct. 19, 2020 and entitled "Point of Collection qPCR System." This application is also related to PCT applications entitled "Method and Apparatus for Controlling Fluid Volumes to Achieve Separation and PCR Amplification," "Disposable Cartridge for Reagent Storage and Methods Using Same," and "Apparatuses with Fluidic Channel Geometries for Sample to Answer PCR Analysis and Methods of Using Same," and a U.S. Design application Ser. No. 29/812,034 entitled "Fluidic Channel Geometries of a Chip," all filed concurrently on Oct. 19, 2021 and listing the same Applicant, Formulatrix, Inc. The contents of the above application are all incorporated by reference as if fully set forth herein in their entireties.

FIELD

The present invention relates to real-time polymerase chain reaction, (qPCR), systems and methods, namely, PCR system and methods for improving the functionality of qPCR processing and analysis through optical and electrical detection of a sample.

BACKGROUND

Real time polymerase chain reaction (real-time PCR), also known as quantitative PCR or (qPCR), is a technique that monitors amplification of a targeted DNA during real time, that can be used in quantitative analysis, rather than at the end of a polymerase chain reaction (PCR) procedure. There are two common methods for detection of PCR products in real time. The first is non-specific fluorescent dyes that intercalate with DNA, the second is sequence specific DNA probes, comprising oligonucleotides that are labelled with a fluorescent reporter, which permits detection only after hybridization of the probe with its complementary sequence.

Reverse transcription polymerase chain reaction (RT-PCR) is a technique of combining reverse transcription of RNA into DNA, complimentary DNA, also known as cDNA, and amplification of specific DNA targets. In combining RT-PCR with qPCR (RT-qPCR), technicians can analyze gene expression and quantification of viral RNA.

Historically, the process of performing RT-qPCR required a skilled technician, along with sophisticated and expensive equipment. The disclosure herein provides improvements to systems and methods of laboratory techniques for performing RT-qPCR by adding mechanical, computational, and biological functionality that advance the capability of quantitative analysis. Further, systems and methods of error checking, fluidic detection, and tracking allow improvements in consumable chip analytics by controlling error detection, tracking, and motor function, along with sample speed and sample integrity.

SUMMARY

Systems and methods for detecting and making real-time adjustments to positional control on a fluidic volume are disclosed herein. The fluidic volume may be located within a chip with a membrane, wherein a cycling is performed for RT-qPCR.

In some embodiments, for example, a system for detecting and making real-time adjustments to positional control of a fluidic volume moving through an optical detection region in a fluidic channel is disclosed. The system includes a mechanical instrument. It is further configured with a chip comprising a fluidic channel, wherein the mechanical instrument controls the motion of the fluidic volume. Lastly, the chip is further comprised of an optical detection region that may contain a voxel. The system is further equipped with one or more independent heat blocks. The chip is positioned at least partially on the one or more independent heat blocks so that the fluidic channel is within close proximity to the one or more independent heat blocks. Further, the system is equipped with an optical detection unit that comprises an optical light-emitting element, and at times three light emitting diodes with a dual band filter. The optical detection unit of the system further comprises an optical detector, which may be a plurality of detection diodes, and a processing unit for performing analysis on the optical detection region of the chip.

In additional embodiments, a method for detecting and making real-time adjustments to positional control of a fluidic volume moving through an optical detection region in a fluidic channel is disclosed. The method comprising preparing a sample with a fluorescent marker. Next, configuring a chip to receive the sample, wherein the chip has a fluid channel for the sample to flow along, and an optical detection region that allows for optical light transmission to the fluid channel. Next, applying the sample to the chip and applying the chip to two heating arrays. Then, initiating an optical detection unit, wherein initiating the optical detection unit is configured to illuminate one or more LED's and to activate an optical detection diode. Next, initiating a mechanical instrument to depress regions of the chip, wherein the depressed regions cause the fluid within the chip, including the sample, to move along the fluidic channel and across the two heating arrays. Then detecting, by the optical detection unit, presence of the sample and signal output of the sample within the optical detection region. The method then adjusting a motion control script based on at least the signal output, wherein the motion control script adjusts at least a start and/or stop of the mechanical instrument.

In further embodiments, a method for detecting and making real-time adjustments to positional control of a fluidic volume moving in a fluidic channel is disclosed. The method comprising, preparing a sample with magnetic beads that attract nucleic acid compounds. Next, configuring a chip to receive the sample, wherein the chip has a fluid channel for the sample to flow along, and the fluid channel crosses two separate heating arrays. Next, applying the sample to the chip and applying a capacitive array along sections of the fluid channel of the chip, also known as capacitive sensing regions. Next, initiating a mechanical instrument to depress regions of the chip, wherein the depressed regions cause the fluid within the chip, including the sample, to move along the fluidic channel and across the two separate heating arrays. The method then detecting, by capacitive sensors within the capacitive sensing region, capacitance change in the fluid channel at the capacitive array.

BRIEF DESCRIPTION OF THE DRAWINGS

Many aspects of the present disclosure can be better understood with reference to the following drawings. The components in the drawings are not necessarily to scale, with emphasis instead being placed upon clearly illustrating the principles of the disclosure. Moreover, in the drawings, like reference numerals designate corresponding parts throughout the several views. In the drawings.

DETAILED DESCRIPTION

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Figure 1:
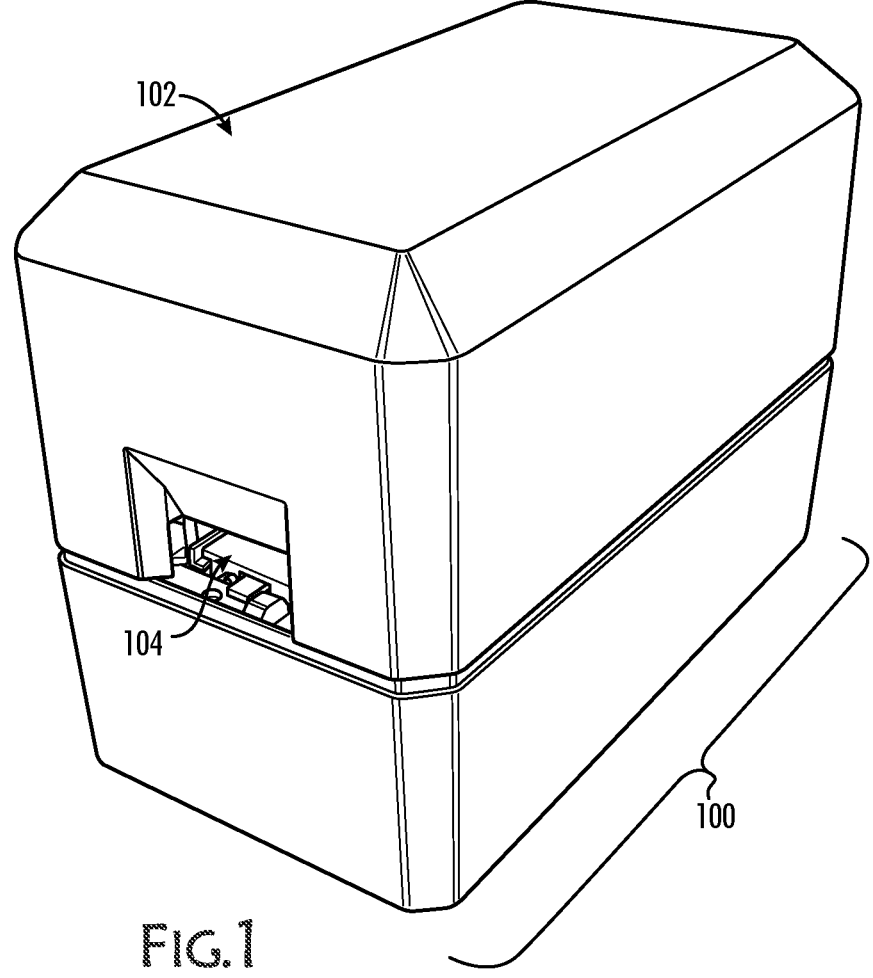
FIG. 1 is an illustration of an example embodiment of a fluidic RT-qPCR system for RT-qPCR analysis.

Referring now to FIG. 1, an example embodiment of a fluidic RT-qPCR system 100 is disclosed. The housing 102 protects the internal elements, including the mechanical instrument for pushing pins into the membrane of a chip through a cartridge, as well as the processing equipment. Not depicted, is a display unit or screen for displaying a graphical user interface to a technician utilizing the fluidic RT-qPCR system 100, built within the housing 102. The cartridge or consumable cartridge slides into the cartridge insert 104 within the housing. The chip is configured within the cartridge, where a sample and/or fluid is first placed on the chip, and then the chip is inserted into the cartridge insert 104. Dimensions for the system range in size from 12 inches to 36 inches in height and width, and may be configured to fit within an existing laboratory environment by positioning the internal hardware elements in a varying array of configurations. For purposes of this disclosure a sample and fluid may be used interchangeably.

As discussed, the qPCR system is a real-time qPCR system (RT-qPCR), wherein the sample is observed in real-time as the amplification procedure is conducted. The fluidic RT-qPCR system 100 is designed to handle many of the tasks which may have traditionally been performed by a technician. The chip for insertion to the cartridge is consumable, allowing single use and disposal in compliance with various regulations and/or protocols.

Figure 2:
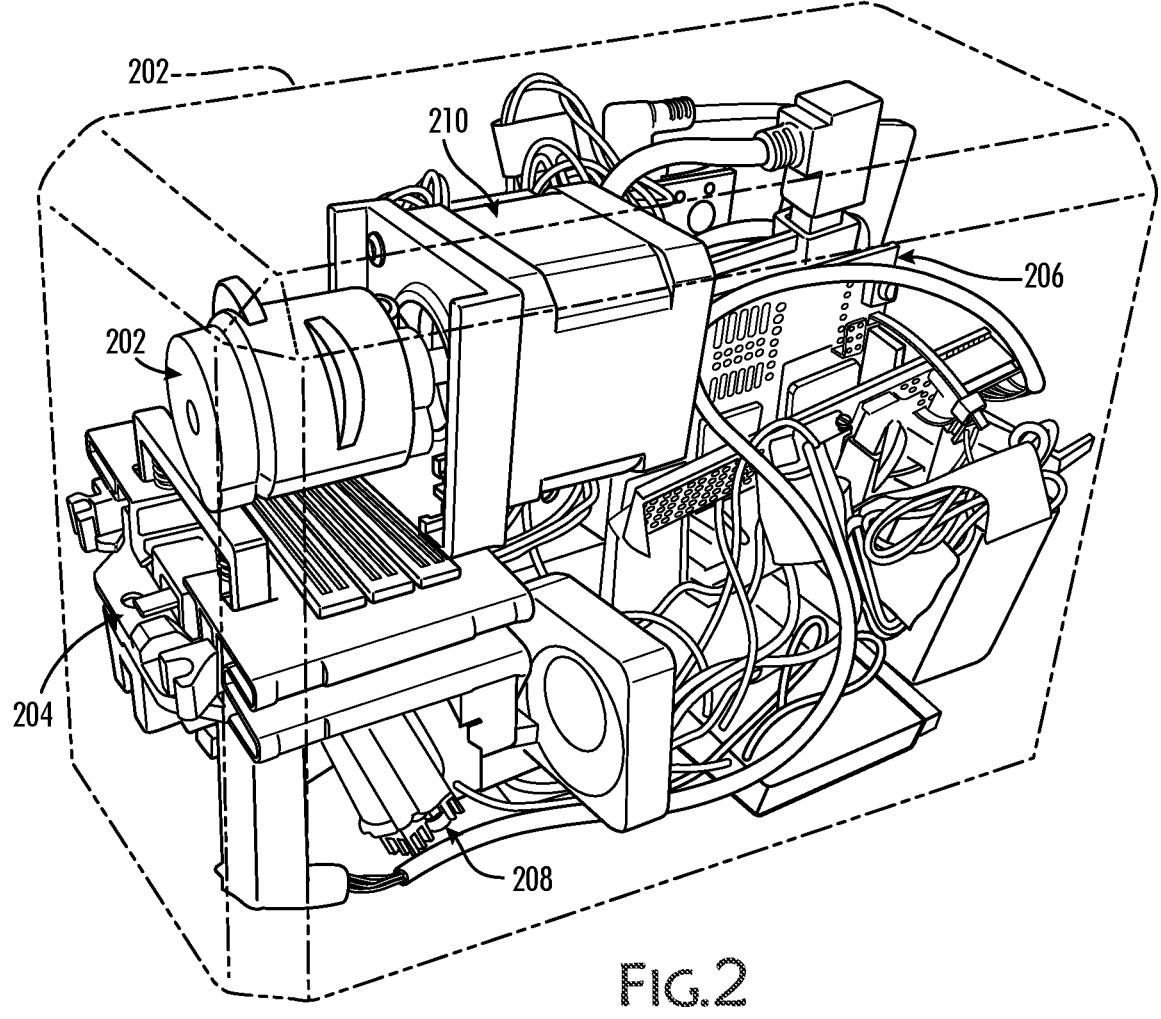
FIG. 2 is an illustration of an example embodiment of the housing removed of FIG. 1, for a fluidic RT-qPCR system.

Referring now to FIG. 2, an illustration of an example embodiment of the housing removed of FIG. 1, for a fluidic RT-qPCR system for RT-qPCR analysis. In the example, a mechanical instrument 202 orbits around a central axis. The mechanical instrument is equipped with nodes or ridges, wherein orbiting the nodes or ridges impact a set of pins, the pins press onto a rubber membrane of a chip, thus allowing fluid trapped within the chip to be cycled to different zones. The differing zones including heating regions, magnet regions, and capacitive array regions. A further elaboration of the various zones of an example chip are disclosed in FIG. 5. The mechanical instrument may be an overhead drum, a drum, or a cam that is rigid in nature with a smooth exterior and nodules for depressing pins onto the surface membrane of a chip. The overhead drum or cam may be comprised of a metal or hard polymer; further, the motor configured to the mechanical instrument allows for start and stop, as well as changing the acceleration and velocity of the drum. The motor connects through a shaft or a gearbox to drive the overhead drum or cam. Input received from the optical detection unit, and/or the capacitance array, allows for configuration of a control algorithm for the mechanical instrument 202.

In some example, an algorithm is defined within the logic of the processing unit, wherein a certain measure of analog to digital (ADC) counts on a fluorescent marker may send a feedback look to either stop the mechanical instrument after a specified time, such as ten seconds from passing the optical detection region. Similarly, the mechanical instrument may be triggered to begin rotation around the central axis when ADC counts have cleared the voxel or an optical detection region and have spent a specified period of time on a heating unit. For the disclosure herein, a heating unit, a heating block, a heating zone, or a heating element mean the same thing, and in some example multiple heating elements, each with a varied temperature range may be a part of an embodiment.

Continuing, a consumable cartridge, a cartridge that may also be disposed or recycled, is placed into a consumable cartridge insert 204 within the system, where the cartridge is aligned with the various pins oriented beneath the mechanical instrument 202. As the motor 210 engages, in response to either the processing unit or system pre-defined function, or as part of the initial system parameters, the mechanical instrument 202 turns around a central axis, the ridges press the pins to cycle fluid within the fluidic channel of a chip. The sample being deposited within the chip, and the chip being configured with a plurality of wash solutions, as well as areas for depositing waste fluid.

The processing unit may be equipped on a single PCB board and may have multiple components such as a GPU, RAM, SSD, along with peripherals and I/O for additional input and output to peripheral devices. It is contemplated that the system herein may communicate over a data cable or through wireless protocols, and may be adapted and configured to a cloud environment where a cluster of devices may form a system that can perform diagnostics and testing on a plurality of devices.

In one example, the sample may be prepared with a fluorescent marker (dye), such as that of FAM™, HEX™, ROX™, TET™, JOE™, VIC™, NED™, PET™, TAMRA™, or any other fluorescent dye utilized in DNA sequencing. Many of these dyes are excited at a single wavelength of 488 nm, but emit at distinctly different wavelengths. The table below provides examples of various fluorescent dyes that may be incorporated within the disclosure herein.

TABLE 1

Example of Fluorescent Dye

| Name | $\lambda_{max}$/nm (absorption) | $\lambda_{max}$/nm (emission) |
|---|---|---|
| FAM ™ | 494 | 518 |
| HEX ™ | 535 | 556 |
| ROX ™ | 575 | 602 |
| TAMRA ™ | 555 | 580 |
| JOE ™ | 520 | 548 |

In another example, the sample may be prepared with magnetic beads, or beads for preparation of a DNA sample, such as those manufactured by ACRO Biosystems™ for binding to nucleic acid compounds. There are a multitude of manufacturers of magnetic beads, and the beads may be selected for properties that fit the specific sample to be analyzed. In yet another example, the sample may have both the fluorescent marker/dye and magnetic beads applied for further processing and utilization of the optical detection system and the capacitive and magnetic arrays as further disclosed herein.

System parameters for a processing unit 206 that drives the system, including the mechanical instrument 202, may be the start and stop time, the length of a cycle, where a cycle is the amount of time the mechanical instrument is in motion, the acceleration of the mechanical instrument, the velocity of the system instrument, as well as many other settings such as the temperatures of the various heating regions, the power to the capacitive regions, the setting for the optical detection unit, as well as other parameters as disclosed herein.

Figure 3:
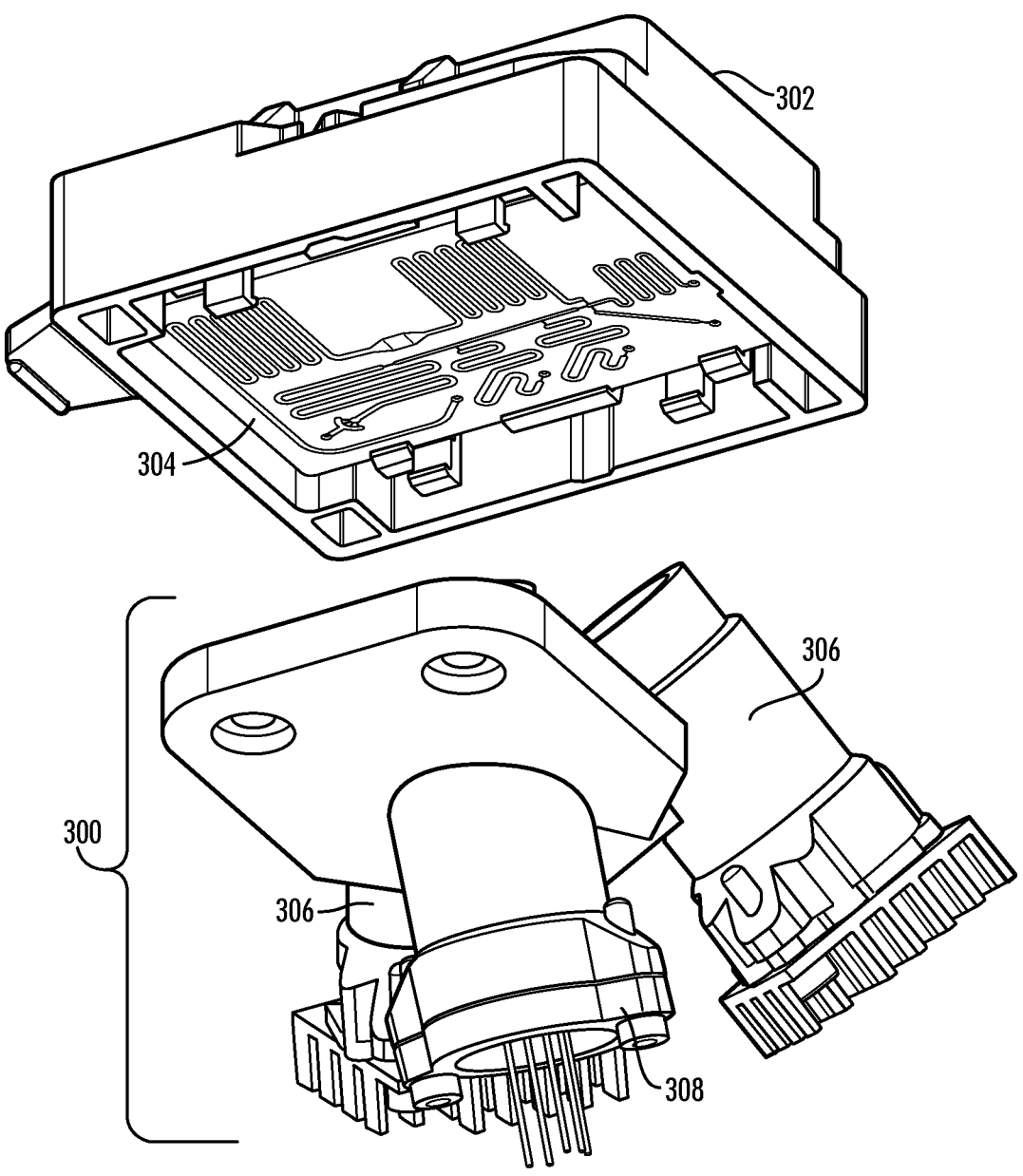
FIG. 3 is an illustration of an example embodiment of an optical detection unit.

Referring now to FIG. 3, an illustration of an example embodiment of an optical detection unit 300. An optical detection unit 300 is configured below the cartridge 302, which houses the chip 304, wherein the prepared sample is placed. Depicted on the chip 304 is a fluidic channel in which the mechanical instrument, through interaction with pins on the rubber membrane on the surface of the chip will move the sample and other fluids to specific regions or zones within the chip. Not depicted in the example of FIG. 3 are the heating regions or heating zones, along with respective heating units, the magnetic zone and the capacitive arrays and zones. These elements are positioned on the bottom of the chip and correspond to the various functionality disclosed herein. For example, the serpentine pathway on the left and right side of the chip, in one example, is situated over two separate heating elements. One element comprising a hot region or zone (95-98 C) on the fluidic channel and a cool region (55-60 C) on the fluidic channel. The hot region forming a first heating block or unit, and the cool region forming a second heating block or unit. This type of heating arrangement is utilized for the amplification process.

Between the two heating regions is a voxel or an optical detection region, wherein the optical detection unit is focused for observation of the fluorescent dye within the sample.

The optical detection unit 300, is configured with an optical light-emitting element such as diode 306, an optical detector such as detection diode 308, and a processing unit for performing analysis on the optical detection region of the chip 304. The processing unit may further be configured with an onboard timer, including a system timer for the processor, such timer may be used in determining peripheral device interaction. The optical light-emitting diodes emit at an excitation value for the particular dye or marker within the sample to produce results detectable by the detection diode 308. As a sample moves, by force from the mechanical instrument pushing pins onto the rubber membrane of the chip, the fluid crosses the optical detection region, sometimes referred to as a voxel, wherein the optical detection unit 300 performs analysis on the sample. The voxel and/or optical detection region is an area where the optical detection unit may perform as intended. This type of detection is often referred to as dynamic detection, as the optical detection unit 300 is performing detection as the fluid cycles, and as amplification is occurring in real-time. Therefore, the motor is capable of adjustments of on and off, or a change in acceleration or velocity, while the fluid is being cycled. Therefore, the optical detection unit serves as a control for the motor as well as a verification and detection process of detecting the fluid is traversing between the two heating regions, and the status of amplification. Example light emitting diodes 306, include those manufactured by Lumileds™ such as LED lighting color series Blue 470 nm for dyes or markers with the specific wavelength. Typical current max is 1 amp with a luminous flux of 35 lm and a viewing angle of 125 degrees.

The optical detection unit 300 forms an assembly that may have computational power built within it, or may connect through data cables or wirelessly to a processing unit housed elsewhere on the system. Further, microcontrollers and motors may be applied to the optical detection unit 300 for fine tuning diode angle, or adjusting separation from the chip. Such improvements in moving a unit or assembly will be known to those of skill in the art, that certain refinement in optical imaging requires precision with location of diodes and light emitting sources. Further, any number of diodes may be applied, in this example three optical light emitting diodes are disclosed. However, in other embodiments one, two, or more may be used. Similarly, with the detection diode 308, in this example two detection diodes are disclosed, however, the number of detection diodes will vary with the system goals.

Figures 4A, 4B, 4C, 4D:
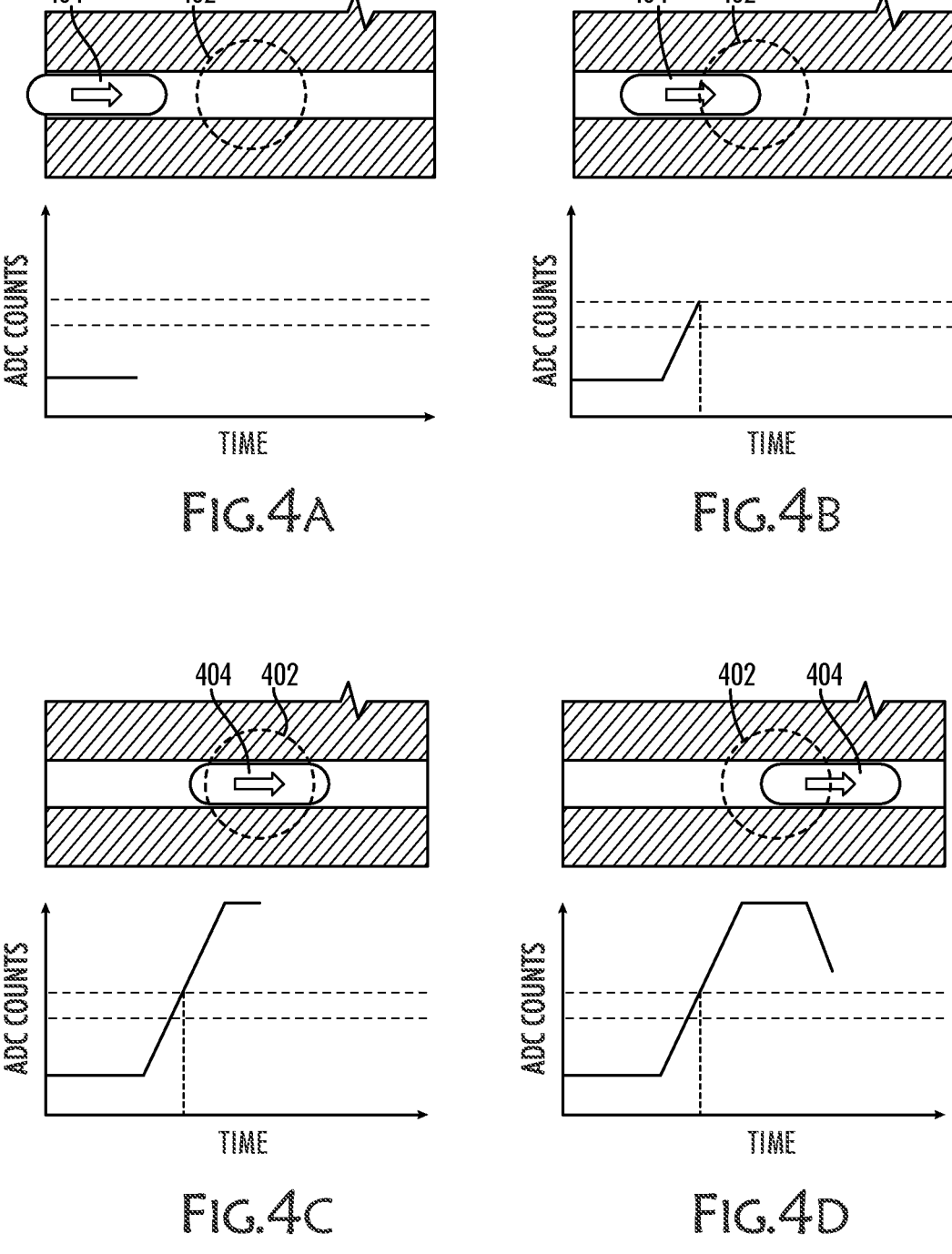
FIG. 4A-E is an illustration of an example embodiment of a sample moving through an optical detection region of a fluidic channel, where the analog to digital (ADC) counts are reflective of position.

Continuing, now referring to FIGS. 4A-E, illustrations of an example embodiment of a sample moving through an optical detection region of a fluidic channel, where the analog to digital (ADC) counts are reflective of position. In FIG. 4A, the sample 404 is moving through the fluidic channel of the chip, and is shown moving from one heating region to another heating region by the mechanical force on the membrane of the chip causing air within the chip to move the sample through the fluidic channel. The sample 404 is moving towards the detection region 402, where a voxel is located for better access for the optical detection unit. A light emitting diode is placed to direct light up to the bottom side of the chip where the sample 404 is moving. As the sample 404 has not reached the optical detection region 402, the ADC counts remain at a baseline.

In FIG. 4B, the sample 404 begins entering the optical detection region 402, and ADC counts begin to increase. This increase is due to the diode reflecting off the fluorescent dye or marker, and the diode receiving more counts. In FIG. 4C, the sample 404 is centered on the optical detection region 402, and ADC counts peak. This reading informs the system the sample is within the voxel or that a majority of the sample is moving towards the next heating region. The motor may be controlled to run until counts drop, or to pause for additional readings at the optical detection region 402. In FIG. 4D, the sample 404 is moving out of the optical detection region, indicating that the sample is moving towards the heating element and away from the voxel. At this stage ADC counts begin to drop, and a distinct sinusoid wave or curve is formed to indicate sample movement. This information is then utilized to inform a technician as well as the motor on relative positioning of the sample, the status of the system, and the amount of cycles performed.

Figures 4E, 5:
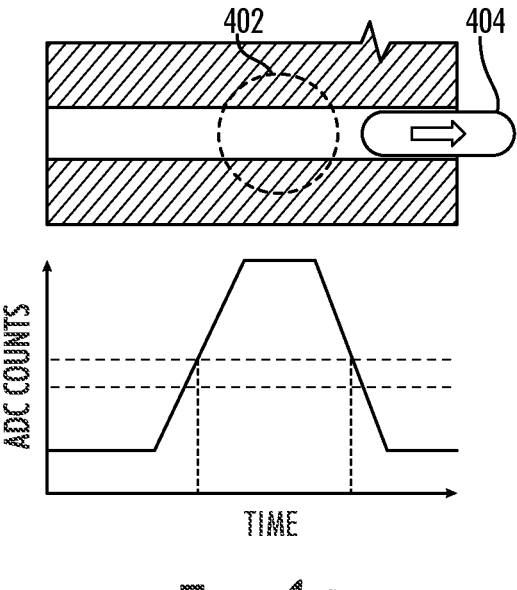
FIG. 5 is an illustration of an example embodiment of a chip.

In FIG. 4E, the sample 404 has egressed through the optical detection region 402 and is entering a heating region, or is within a capacitive array region, or is progressing along the fluidic channel as prescribed. If the sample 404 is not detected with a similar curve the system may alert a technician or throw an error that the sample 404 is not being cycled, or that the run needs to start again. The curve forming from the amount of counts over time, indicating movement of the sample. Failure of the ADC counts may include the sample 404 stalling or a leak or failure in the chip, thus indicating the system is not operating and initiating an error message or alert, either through a visual or audible indicator.

Referring now to FIG. 5, an illustration of an example embodiment of a chip. The fluidic channel navigates throughout the chip, and in this example the orientation is unique for the capacitive array and optical detection unit. Additional chip designs and ornamentation are contemplated, so long as the principals disclosed herein remain, and such additional configurations form a part of this disclosure. On the top side of the chip is a rubber membrane, which may consist of rubber or other material that allows flex when contacted by pins being driven by a motor attached to a mechanical instrument, such as a mechanical drum or cam. The chip may also comprise several other layers, such as a capacitive layer, and layers for insertion of probes or other diagnostics.

In the example of FIG. 5, the sample start 512 is where the sample first enters the chip from the cartridge and begins the process. The mechanical instrument moves the sample through the sequence of channels to a fluid hub 508. The fluid hub may contain a magnet or other apparatus to hold the fluid in the fluid hub 508. Next, a magnetic region 506, which is designed when the sample is prepared with magnetic beads to hold portions of the sample bound to said beads within the magnetic region 506. On the system may be a magnetic array that accommodates the underside of the chip for purposes of holding the sample or other diagnostic or preparation methods.

In the example of FIG. 5 two heating regions are disclosed, one a hot region and the other a cold region. Temperatures are defined for optimal amplification of DNA. In this example the hot region (95-98 C) and a cool region (55-60 C) are heated to the specific temperatures by two thermal heating units. In other examples one heating element with variability of heating zones may be used, or in additional examples more than two heating elements may be used.

Capacitive liquid sensing arrays 502 are positioned in regions indicated, and in combination with the sample prepare for magnetic beads allows for tracking of fluid within the fluidic channel of the chip. In this example, the capacitive arrays are positioned on either side of the optical detection region or voxel, in doing so relative position of cycling between the two heating regions may be determined. Further, the capacitive liquid sensing arrays are positioned on the entry and exit sides of the heating regions 504, thus allowing full tracking of the sample as it moves through the amplification process. The capacitive arrays may work independently of the optical detection unit, or in combination with, in detecting and transmitting signals or information to a processing unit that controls the motor and mechanical instrument as well as instrumentation such as screens or diagnostics for a technician.

Figure 6:
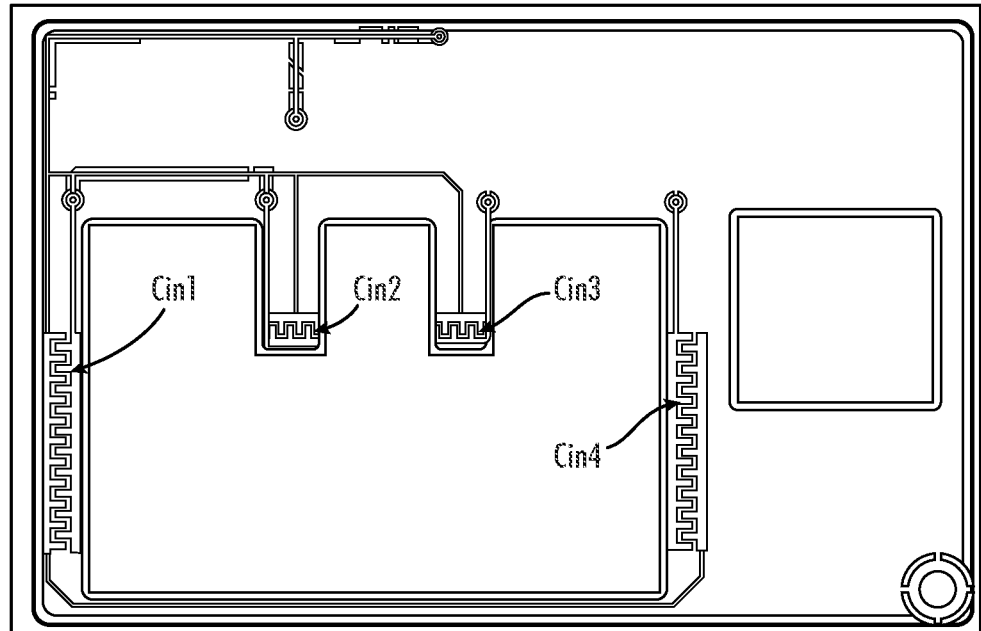
FIG. 6 is an illustration of an example embodiment of a capacitive sensing array for use with a chip.

FIG. 6 is an illustration of an example embodiment of a capacitive array for use with a chip with capacitive sensing regions. The capacitive array being positioned at specific capacitive sensing regions for detecting fluid/sample presence. Examples of such regions were disclosed in FIG. 5. Additional regions may exist and a "blanket" of capacitive sensing may be equipped for comprehensive tracking of the sample. In this example, the sample may be prepared with magnetic beads, such beads allow for tracking utilizing the capacitive sensing array, including a capacitive sensor, covering the capacitive sensing region on the chip. Further, the sample may also be tracked with capacitance of the sample fluid itself, where the sample is tracked with preferential positions at the beginning and end of the heating zones and on both sides of an optical detection region. Additional zones may be specified after a wash period or other location in which an occlusion or block may occur, such capacitive array coupled with a capacitive sensor would allow for detecting, tracking, alerting, and correcting of the sample and RT-qPCR run.

Figure 7:
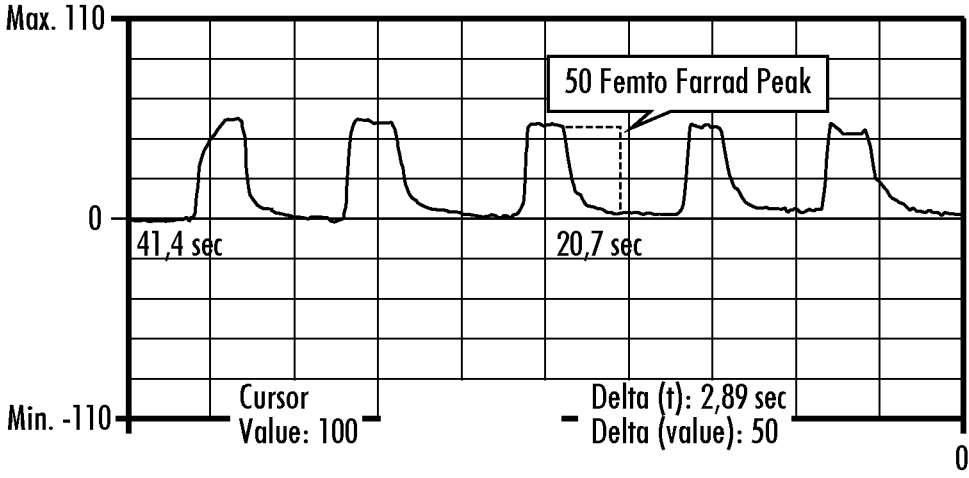
FIG. 7 is a chart of an example embodiment of farads detected when a sample moves through a fluidic channel over a capacitive sensing array.

FIG. 7 is a chart of an example embodiment of farads detected when a sample moves through a fluidic channel over a capacitive sensing array on a capacitive sensing region on a chip. In this example, measurement detects a peak at 50 femto Farad when the sample and/or fluid is distributed over the capacitive array, and is sensed by the capacitive array and transmitted to a processing unit. The processing unit equipped with a processor capable of executing programmatic instructions, and defining an algorithm for movement of the motor in accordance with feedback from the capacitive array and/or the optical detection unit.

The chart in FIG. 7 indicating the sample is being moved back and forth across a capacitive sensing array, thus the system is performing as expected. Where the sample and/or fluid is absent the Farad reading, returning to baseline, and as the sample passes forming a sine type of wave. This is relative to motor speed and intensity as the sample is moved from one heating region to the other. The capacitive sensing array may also provide feedback to the motor, controlling the start and stop, as well as the velocity and acceleration.

Figure 8:
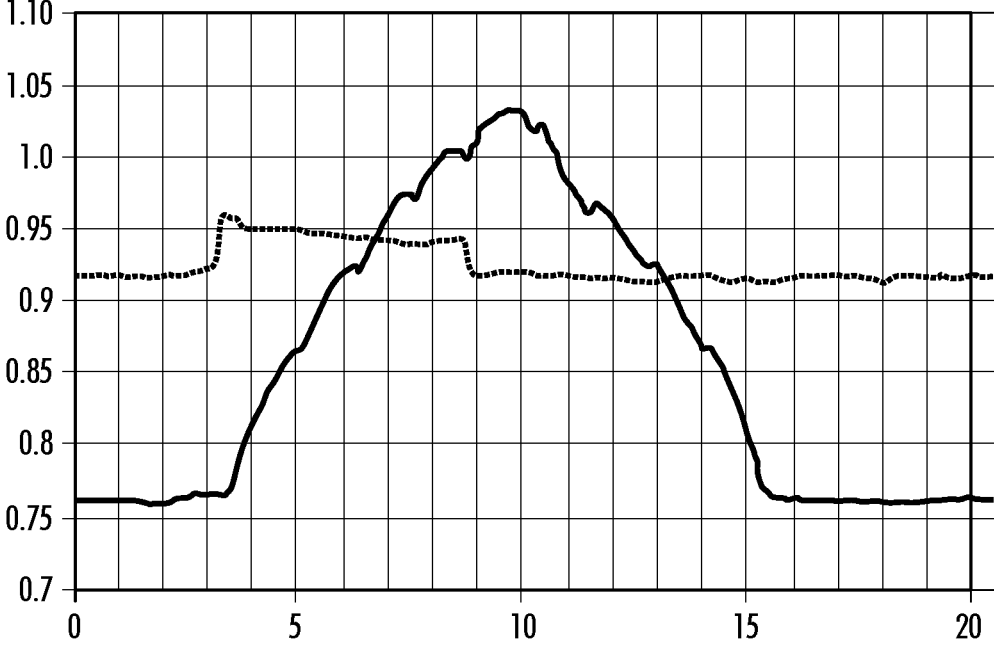
FIG. 8 is a chart of an example embodiment representing capacitive signal.

FIG. 8 is a chart of an example embodiment representing capacitive signal. In the example of FIG. 8, the capacitive array covers the entire serpentine channel of the heating regions, as defined more fully in the example of FIG. 5 on the chip. The capacitance is shown as the sample is located over the sensing array and as it leaves the array tapering off. This allows manipulation through filtering of noise, but also usage of signal strength for controlling the motor unit or supplying diagnostics on the RT-qPCR run.

Figure 9:
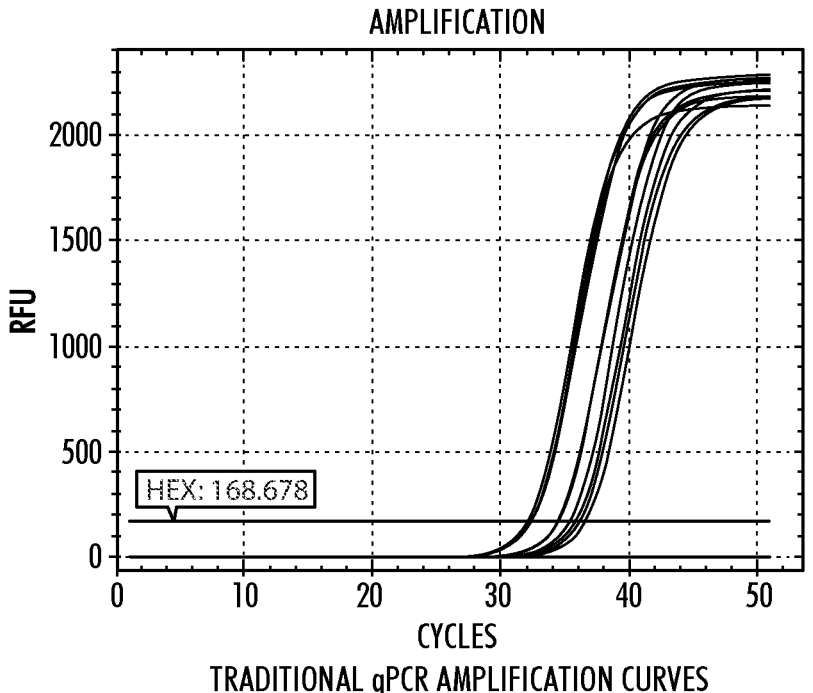
FIG. 9 is a chart of an example embodiment of RT-qPCR amplification time of traditional cycling.

FIG. 9 is a chart of an example embodiment of RT-qPCR amplification time of traditional cycling. Amplification of the target within the sample is disclosed along with an average timeline of cycles.

Figure 10:
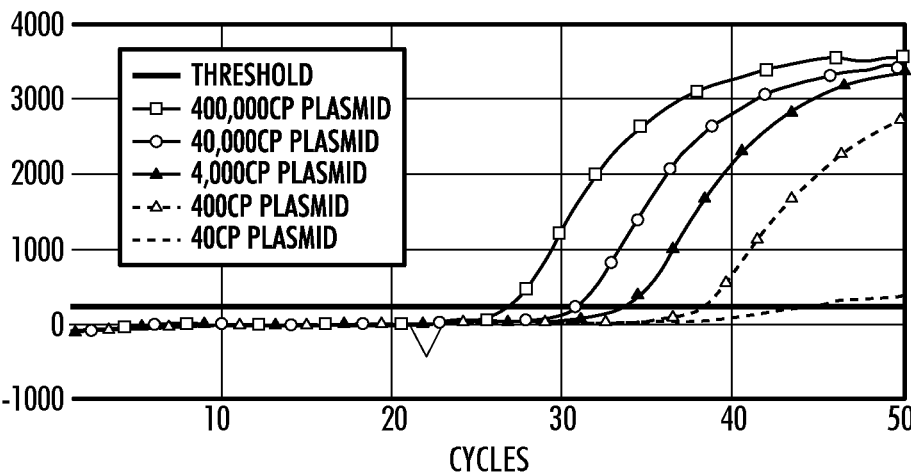
FIG. 10 is a chart of an example embodiment of the functionality disclosed herein in improving the time of RT-qPCR amplification.

FIG. 10 is a chart of an example embodiment of the functionality disclosed herein in improving the time of RT-qPCR amplification. The system benefits from the feedback loop established from the optical detection unit, and the capacitive array, in coordination with the motor and mechanical instrument. Thus, allowing a chip insert, to remain protected, while also being monitored for progression through the cycles. Therefore, the disclosures herein further provide systems and methods for detecting and making real-time adjustments to positional control of a fluidic volume, such as a sample, moving through an optical detection region and/or a capacitive region in a fluidic channel of a chip. In one example, real-time adjustments are made through coordination with the optical detection unit, and the capacitive array sensor, allowing for coordinated feedback and an algorithm to control motor function of the mechanical instrument. The outcome results in reliable, and fast RT-qPCR amplification and analysis, in a self-contained system that may rapidly run results with little to no technician training.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

The term "plurality" means "two or more".

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A system for detecting and making real-time adjustments to positional control of a fluidic volume moving through an optical detection region in a fluidic channel, comprising:
    a mechanical instrument;
    a chip, comprising:
        (i) a fluidic channel, wherein the mechanical instrument controls the motion of a fluidic volume; and
        (ii) an optical detection region;
    one or more independent heat blocks, wherein the chip is positioned at least partially on the one or more independent heat blocks so that the fluidic channel is within close proximity to the one or more independent heat blocks;
    an optical detection unit, comprising:
        (i) an optical light-emitting element;
        (ii) an optical detector; and
        (iii) a processing unit for performing analysis on the optical detection region of the chip, comprising detecting the presence of a sample and signal output of the sample within the optical detection region, and wherein the processing unit adjusts a motion control script based on at least the signal output, wherein the motion control script adjusts at least a start and/or stop of the mechanical instrument.

2. The system of claim 1, wherein the mechanical instrument is an overhead drum, and the overhead drum is positioned to depress pins onto a rubber membrane of the chip for fluidic control.

3. The system of claim 1, further comprising a housing for containing the mechanical instrument, the chip, and the optical detection unit.

4. The system of claim 1, the chip further comprising a voxel within the optical detection region.

5. The system of claim 1, further comprising a motor configured to the processing unit, wherein the motor controls the mechanical instrument, which in turn exerts fluidic control through the fluid channel of the chip.

6. The system of claim 5, wherein the processing unit further comprises a timer for recording time and motor position of the motor.

7. The system of claim 1, wherein the optical light emitting element is transmitting light to the detection region of the chip, wherein the optical detector is equipped to detect a fluorescent dye (FAM, HEX, ROX, JOE, TAMRA) from the fluid within the detection region of the fluid channel of the chip.

8. The system of claim 1, further comprising a hot region (95-98 C) on the fluidic channel and a cool region (55-60 C) on the fluidic channel, wherein the hot region is on one of the one or more heating blocks, and the cool region is on a different heating block of the one or more heating blocks.

9. The system of claim 1, wherein the optical detection system is on a single PCB board.

10. The system of claim 1, further comprising three optical light-emitting diodes and two dual-band filters.

11. The system of claim 1, further comprising capacitive sensing regions on the chip and capacitive sensing arrays configured to detect presence of the sample and to electrically communicate with the processing unit.

12. A method for detecting and making real-time adjustments to positional control of a fluidic volume moving through an optical detection region in a fluidic channel, comprising: preparing a sample with a fluorescent marker;

configuring a chip to receive the sample, wherein the chip has a fluid channel for the sample to flow along, and an optical detection region that allows for optical light transmission to the fluid channel;

applying the sample to the chip;

initiating an optical detection unit, wherein initiating the optical detection unit is configured to illuminate one or more LED's and to activate an optical detection diode;

applying the chip to two heating arrays;

initiating a mechanical instrument to depress regions of the chip, wherein the depressed regions cause the fluid within the chip, including the sample, to move along the fluidic channel and across the two heating arrays;

detecting, by the optical detection unit, presence of the sample and signal output of the sample within the optical detection region; and adjusting a motion control script based on at least the signal output, wherein the motion control script adjusts at least a start and/or stop of the mechanical instrument.

13. The method of claim 12, wherein configuring the chip to receive a sample, further configures the chip with: (i) rubber membranes on a surface of the chip, (ii) a plurality of fluidic channels, (iii) a hot fluidic channel region, (iv) a cold fluidic channel region, and (v) one or more capacitive sensing regions.

14. The method of claim 12, further comprising applying the chip to a capacitive liquid sensing array, wherein the capacitive liquid sensing array measures change in capacitance for detecting the presence of fluids a particular region of the fluidic channel on the chip.

15. The method of claim 12, wherein adjusting the motion control script further adjusts at least velocity and/or acceleration of the mechanical instrument.

16. A method for detecting and making real-time adjustments to positional control of a fluidic volume moving in a fluidic channel, comprising:

preparing a sample with magnetic beads that attract nucleic acid compounds;

configuring a chip to receive the sample, wherein the chip has a fluid channel for the sample to flow along, and the fluid channel crosses two separate heating arrays;

applying the sample to the chip;

applying a capacitive array along sections of the fluid channel of the chip;

initiating a mechanical instrument to depress regions of the chip, wherein the depressed regions cause the fluid within the chip, including the sample, to move along the fluidic channel and across the two separate heating arrays; and detecting, by capacitive sensors, capacitance change in the fluid channel at the capacitive array.

17. The method of claim 16, further comprising adjusting a motion control script based on at least signal output from the capacitive array, wherein the motion control script adjusts the velocity and/or the acceleration of the mechanical instrument depressing pins into regions of the chip.

18. The method of claim 16, wherein detecting, by the capacitive sensors, capacitance change, indicates the presence of the sample within the fluid channel at the specific region of the capacitive array.

19. The method of claim 16, further comprising preparing the sample with a fluorescent marker.

20. The method of claim 19, further comprising initiating an optical detection unit, wherein initiating the optical detection unit is configured to illuminate one or more LED's and to activate an optical detection diode.

21. The method of claim 16, further comprising initiating a hot region (95-98 C) on the fluidic channel and a cool region (55-60 C) on the fluidic channel, wherein the hot region is a first heating block, and the cool region is a second heating block.

\* \* \* \* \*